US006623729B2

(12) United States Patent
Park et al.

(10) Patent No.: US 6,623,729 B2
(45) Date of Patent: Sep. 23, 2003

(54) PROCESS FOR PREPARING SUSTAINED RELEASE MICELLE EMPLOYING CONJUGATE OF ANTICANCER DRUG AND BIODEGRADABLE POLYMER

(75) Inventors: Tae Gwan Park, Taejon (KR); Hyuk Sang Yoo, Taejon (KR)

(73) Assignee: Korea Advanced Institute of Science and Technology, Taejon (KR)

( * ) Notice: Subject to any disclaimer, the term of this patent is extended or adjusted under 35 U.S.C. 154(b) by 0 days.

(21) Appl. No.: 09/902,549

(22) Filed: Jul. 9, 2001

(65) Prior Publication Data

US 2003/0017131 A1 Jan. 23, 2003

(51) Int. Cl.$^7$ .................. A61K 47/48; A61K 31/74; A61K 31/785; A61K 9/14
(52) U.S. Cl. .................. 424/78.17; 424/78.07; 424/78.36; 424/78.37; 424/426; 424/486; 424/489; 424/497
(58) Field of Search .............. 424/78.08, 78.17, 424/78.36, 78.37, 426, 486, 489, 497; 525/408, 411, 413, 415; 528/354, 359

(56) References Cited

U.S. PATENT DOCUMENTS 6,322,805 B1 * 11/2001 Kim et al. ................. 424/426

OTHER PUBLICATIONS

Yokoyama et al. "Preparation of micelle–forming Polymer–Drug Conjugates." Bioconjugate Chem., 3(4):295–301(1992).*
Yoo, H.S., et al., "Biodegradable Polymeric Micelles Containing Doxorubicin Conjugated PLGA–PEG Block Copolymers." Controlled Release Society, Inc., 27$^{th}$ International Symposium (2000).

Yoo, H.S., et al., "Biodegradable Nanoparticles Containing Doxorubicin–PLGA Conjugate for Sustained Release." Pharmaceutical Research, 16(7):1114–1118 (1999).
Lavie, E. et al., "Monoclonal Antibody L6–daunomycin Conjugates Constructed to Release Free Drug at the Lower pH of Tumor Tissue." Cancer Immunol. Immunother. 33:223–230(1991).
Yokoyama, M., et al., "Preparation of micelle–Forming Polymer–Drug Conjugates." Bioconjugate Chem., 3(4):295–301(1992).
Kaneko, T., et al., "New Hydrazone Derivatives of Adriamycin and Their Immunoconjugates—A Correlation Between Acid Stability and Cytotoxicity." Bioconjugate Chem., 2(3):133–141(1991).
Kwon, G.S., et al., "Physical Entrapment of Adriamycin in AB Block Copolymer Micelles." Pharmaceutical Research, 12(2):192–195(1995).
Kwon, G., et al., "Block Copolymer Micelles for Drug Delivery: Loading and Release of Doxorubicin." J. Control. Release, 48:195–201(1997).

* cited by examiner

Primary Examiner—Thurman K. Page
Assistant Examiner—Blessing Fubara
(74) Attorney, Agent, or Firm—Knobbe Martens Olson & Bear LLP

(57) ABSTRACT

The present invention relates to a process of preparing a sustained release micelle by copolymerizing a biodegradable polyester hydrophobic polymer and a hydrophilic polyethylene glycol (PEG) to obtain a block copolymer, reacting the block copolymer with a linker to the hydroxyl group of the block copolymer and conjugating the linker-bound block copolymer to a drug to obtain a micelle monomer, and dispersing the micelle monomer an aqueous solution. The drug-micelle conjugate of the present invention has practical application in anticancer therapy.

36 Claims, 6 Drawing Sheets

PLGA + mPEG

PLGA + mPEG

PROCESS FOR PREPARING SUSTAINED RELEASE MICELLE EMPLOYING CONJUGATE OF ANTICANCER DRUG AND BIODEGRADABLE POLYMER

FIELD OF THE INVENTION

The present invention relates to a process for preparing sustained release micelle employing a conjugate of anticancer drug and biodegradable polymer, more specifically, to a process for preparing sustained release micelle by conjugating a biodegradable polymer to a drug such as anticancer agent, and a sustained release micelle prepared by the process.

BACKGROUND OF THE INVENTION

In general, polymers used for drug delivery are required to be biosynthetic or biodegradable. Representative polymers satisfying these requirements are aliphatic polyesters containing polyester bonds, which are under FDA approval and used widely as a drug delivery carrier or a suture. Examples of the aliphatic polyesters include polylactic acid (PLA), polyglycolic acid(PGA), poly(D,L-lactic-co-glycolic acid)(PLGA), poly(caprolactone), poly(valerolactone), poly(hydroxybutyrate) and poly(hydroxyvalerate). Among the aliphatic polyesters, PLGA, in particular, have been practically employed as biodegradable polymers with a variety of degradation time by controlling the contents of lactic acid and glycolic acid monomers, or by modifying the process of polymerization.

Since the biodegradable polymers are degraded in a certain period of time, they are not harmful to the human body. For example, a polymer such as PLGA is degraded into non-toxic lactic acid and glycolic acid in the body. Therefore, drug delivery carriers made of biodegradable polymers can be applied in the sustained release of drugs. In particular, drugs which should be administered periodically for a long period of time to keep a constant level in blood can be loaded to the drug delivery carrier, whereby the drugs are released in a sustained manner with the degradation of polymer matrices, therefore, such a sustained release mechanism can be applied in a variety of drug formulations.

Drug delivery carriers employed in the sustained release include microspheres, nanoparticles, and micelles. The size of microspheres range from tens to hundreds of micrometers, nanoparticles around hundreds of nanometers, and micelles about one hundred nanometers. Microsphere preparations are used for subcutaneous intramuscular injections to sustain the release of proteins or drugs. Nanoparticle preparations, mainly used for intravenous injection, are employed for the sustained release of drugs, and for the passive targeting of anticancer drugs to solid tumors. Micelle preparations also can be used for similar purposes described above. When nanoparticle or micelle preparations of anticancer drugs are administered, the size of particles ranging from tens to hundreds of nanometers let them penetrate into tumor tissues across the wall of blood vessel which have loosened cell contact, but would not let them penetrate into normal tissues across the wall of blood vessel which have tight cell contact, therefore, the lack of specificity of anticancer drugs can be successfully overcome due to the structural difference.

Meanwhile, one of crucial problems in conventional drug delivery systems is that drugs cannot be released in a sustained manner. That is, conventional drug delivery systems release high amount of drug at the early stage of administration by way of simple diffusion of drug on the surface of carrier, meanwhile, the amount of released drug is decreasing with time, which plays a detrimental role in maintaining a constant level of drug in blood. Furthermore, in order to load drugs into the carrier sufficiently, large amount of drugs are required, which eventually causes significant drug loss usually up to 50% in the course of loading (that is, in the preparation or formulation). In this respect, much research effort is being devoted to the improvement of loading efficiency.

Drugs such as doxorubicin, adriamycin, cisplatin, taxol, and 5-fluorouracil are being widely used in chemotherapies for the treatment of cancer. However, the said anticancer drugs cannot be administered with a large amount due to severe side effects, and give pains to the patients even with as little as effective concentration. Such side effects are mainly caused by the lack of specificity of anticancer drugs, that is, the anticancer drugs not only kill cancer cells but also inhibit normal cell growth and eventually lead to necrosis of normal cells.

Therefore, if an anticancer drug can destroy cancerous cells selectively, it would be administered with a high amount, and effectively applied in the treatment. To achieve this goal, the techniques of drug targeting to cancer cells have been commonly used until now, in which therapeutic agents are linked to a receptor which has a high affinity to an antigen specifically expressed on the cancer cells(see: Minko, T. et al., J. Control. Rel., 54:223–233, 1998; Colin de Verdiere, A. et al., Cancer Chemother. Pharmacol., 33:504–508, 1994).

However, it has been found that repetitive administration of such agents activate an excretory pump which facilitates the excretion of anticancer agents absorbed into cells, resulting in the failure of maintaining the effective level of anticancer agents in the cytoplasm and the failure of exerting anticancer activity. In this regard, many efforts to overcome such problems have been made, however, no remarkable results were attained.

Under the circumstances, there are strong reasons for exploring and developing a sustained release preparation without untoward effects.

SUMMARY OF THE INVENTION

The present inventors have made an effort to reduce the side effects due to the lack of specificity of conventional anticancer agents and to prepare sustained release intravenous injectable formulations, and found that the sustained release micelle prepared by conjugating a biodegradable polymer to a drug such as anticancer agent can be practically applied in anticancer therapy in an efficient manner, by loading a high amount of drug while controlling the release rate of drug.

A primary object of the present invention is, therefore, to provide a process for preparing a sustained release micelle employing a conjugate of biodegradable polymer and drug.

The other object of the invention is to provide a sustained release micelle prepared by the process.

BRIEF DESCRIPTION OF THE DRAWINGS

The above, the other objects and features of the invention will become apparent from the following descriptions given in conjunction with the accompanying drawings, in which.

DETAILED DESCRIPTION OF THE INVENTION

Figure 1:
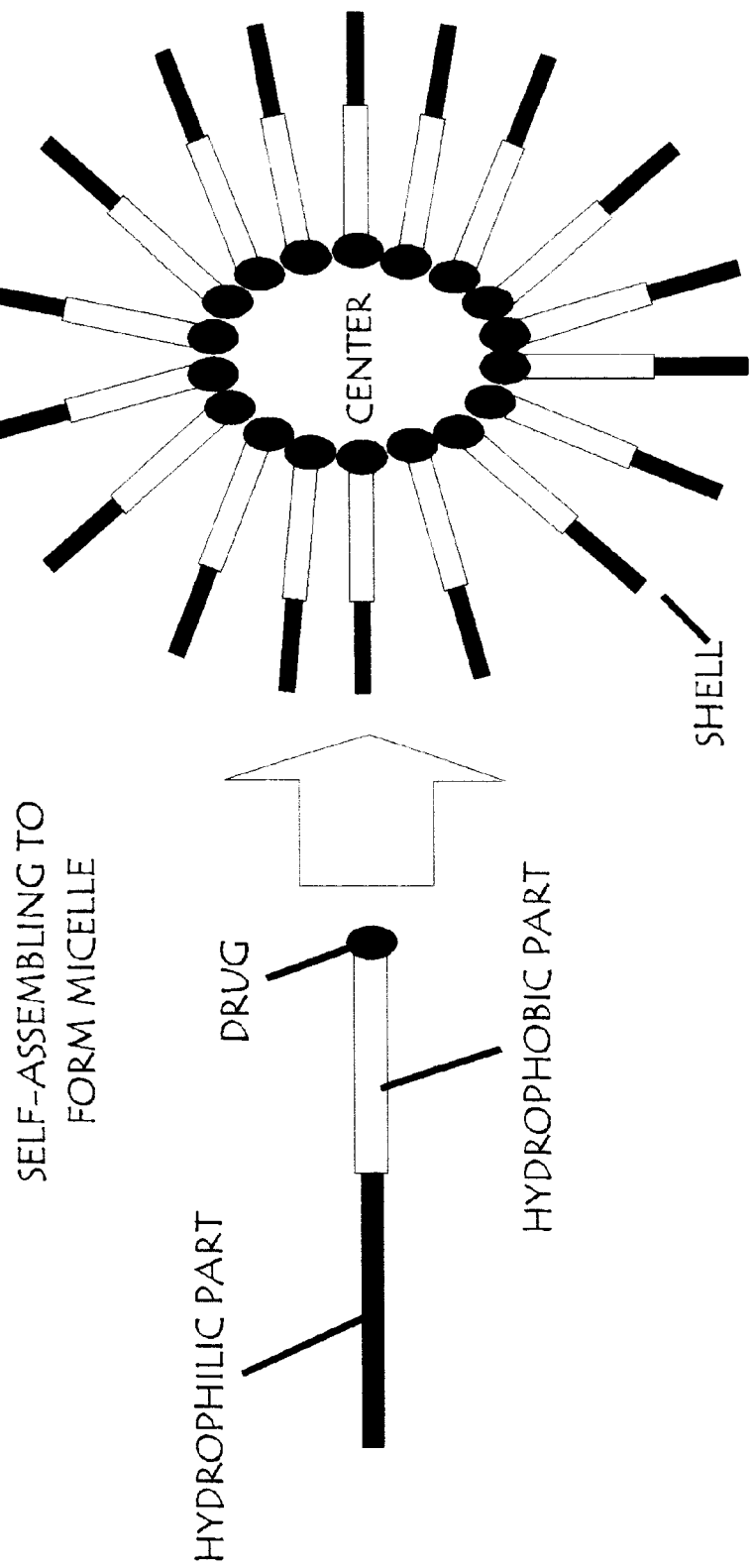
FIG. 1 is a schematic representation of the process for preparing a sustained release micelle of the present invention.

The process for preparing sustained release micelle of the invention comprises the steps of: copolymerizing a biodegradable polyester polymer and a polyethylene glycol(PEG) polymer in the presence of stannous octate at 160–200□ for 2–6 hours under a vacuum condition to obtain a block copolymer containing a hydrophobic part having hydroxyl group at one end and a hydrophilic portion at the other end; reacting the block copolymer dissolved in an organic solvent with a linker in the presence of pyridine and nitrogen at room temperature to bind the linker to the hydroxyl group of block copolymer; conjugating the linker-bound block copolymer obtained by reacting with hydrazine to a drug by covalent bondage to obtain a micelle monomer in the form of a conjugate of drug and block copolymer; and, dispersing the micelle monomer in an aqueous solution (see: FIG. 1).

Process for preparing sustained release micelle of the invention is further illustrated in the following steps:

Step 1: Preparation of Block Copolymer

A block copolymer containing a hydrophobic part having hydroxyl group at one end and a hydrophilic part at the other end is prepared by copolymerization of a biodegradable polyester polymer and a polyethylene glycol(PEG) polymer in the presence of stannous octate as a catalyst: The copolymerization is performed at 160–200□ for 2–6 hours under a vacuum condition. The polyester polymer includes polylactic acid(PLA), polyglycolic acid(PGA), poly(D,L-lactic-co-glycolic acid)(PLGA), poly(caprolactone), poly(valerolactone), poly(hydroxy butyrate) or poly(hydroxy valerate), preferably PLGA, more preferably PLGA which is prepared by reacting glycolic acid and lactic acid with a ratio of 50:50 (molar ratio), and methoxypolyethyleneglycol is preferably used as the polyethyleneglycol polymer.

Step 2: Binding of Linker by an Activation of Functional Groups of Block Copolymer The block copolymer is dissolved in an organic solvent and reacted with a linker at room temperature in the presence of pyridine and nitrogen: The organic solvent includes, but without limitation, methylenechloride, and the linker includes p-nitrophenyl chloroformate, carbonyldiimidazole (CDI), N,N'-disuccinimidyl carbonate(DSC), or a mixture of these compounds, preferably p-nitrophenyl chloroformate. The reaction is carried out for 2 to 6 hours, with a molar ratio of block copolymer:linker:pyridine ranging from 1:2:2 to 1:2:6.

Step 3: Preparation of a Conjugate of Drug and Biodegradable Polymer

The linker-bound block copolymer is conjugated to a drug by covalent bondage to obtain a micelle monomer of a conjugate of drug and block copolymer, where the block copolymer obtained by reacting with hydrazine may be used: The block copolymer reacted with hydrazine forms a micelle monomer by binding the linker to ketone group of drug, while the block copolymer without hydrazine reaction forms a micelle monomer by binding the linker to amine group of drug. Preferably, the drugs include anticancer agents such as, but without limitation, doxorubicin, adriamycin, cisplatin, taxol and 5-fluorouracil.

Step 4: Preparation of Sustained Release Micelle

The micelle monomers prepared in Step 3 are dispersed in an aqueous solution to prepare sustained release micelle. As shown in FIG. 1, when micelle monomers are dispersed in a certain concentration, micelles are formed spontaneously by thermodynamic equilibrium. Sustained release micelles thus prepared release a drug by way of hydrolysis and enzymatic action in vivo, and the released drug exerts the same effect as free drug does.

The sustained release micelles of the invention are characterized as followings: first, drugs are conjugated to the biodegradable polymer by chemical bondage, thus, the efficiency of drug loading is higher than the conventional micelles where drugs are physically entrapped in the polymer; secondly, drug is conjugated to the micelle-forming polymer, such that the micelle structures are spontaneously formed in an aqueous solution; thirdly, drugs can be released in various sustained manners depending on the degradation rate of biodegradable polymers.

Pharmacokinetic properties of the sustained release micelles prepared by the invention are as follows: micellar particulate structure not only let them escape from renal exclusion, but also give them a higher vascular permeability at target sites by passive diffusion; moreover, enhanced uptake of micellar drugs within target cells are expected to occur through an increased endocytosis and a redudhuced multi-drug resistance(MDR) effect; and, water soluble drug-PLGA oligomer fraction is liberated in a controlled manner as a drug-conjugated PLGA backbone is gradually degraded by chemical reaction.

The sustained release micelles containing an anticancer agent of doxorubicin prepared by the invention are compared with the micelles prepared by simple physical mixing of polymer and anticancer drug, which revealed that: higher amount of drugs can be loaded in the sustained release micelles than conventional micelles; and, it exerts increased anticancer effect by releasing anticancer drugs in a sustained manner.

The present invention is further illustrated in the following examples, which should not be taken to limit the scope of the invention.

EXAMPLE 1

Preparation of mPEG-polyester Polymer, mPEG-PLGA 26 g of poly(D,L-lactic-co-glycolic acid) (PLGA) was mixed with 2 g of methoxypolyethylene glycol(mPEG) having a molecular weight of 2000, 8 g of mPEG (MW= 3350), or 16 g of mPEG(MW=8000) in each flask, and each mixture was dissolved thoroughly at 140° C. in the presence of nitrogen gas. Then, 0.05 wt % of stannous octate was added, and reacted at 180° C. for 3 hours. The reaction product was mixed with methylenechloride followed by addition of cold diethylether to give precipitate, which was subsequently filtered, and dried under a reduced pressure to obtain mPEG-PLGA. And then, each molecular weight of mPEG-PLGA thus synthesized were measured by employing gel permeation chromatogrphy(GPC) and a magnetic resonance spectrometer(MRS), and crystallization temperatures were measured by employing differential scanning calorimetry(DSC)(see: Table 1).

TABLE 1

Physicochemical property analysis of mPEG-PLGA

| Polymer | Molecular Weight (Mn) by MRS | Molecular Weight (Mn) by GPC | Molecular Weight (Mw) by GPC | DSC (° C.) |
|---|---|---|---|---|
| PLGA-PEG750 | 8300 | 11000 | 26000 | 21.63 |
| PLGA-PEG3350 | 9600 | 13000 | 23000 | 1.15 |
| PLGA-PEG8000 | 9000 | 9000 | 20000 | −29.89 |

As shown in Table 1 above, three kinds of PLGA-PEG having different molecular weights have been synthesized, respectively. Molecular weights of all the three polymers determined by GPC were above 20,000 and crystallization temperatures determined by DSC decreased with increasing molecular weights of PEG.

EXAMPLE 2

Figure 2:
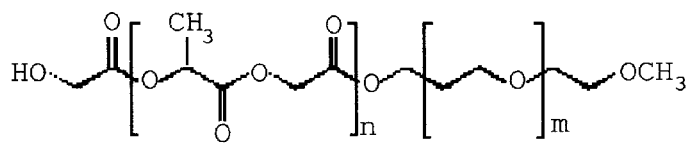
FIG. 2 is a schematic representation of the process for preparing a doxorubicin-conjugated sustained release micelle.
Figure 2:
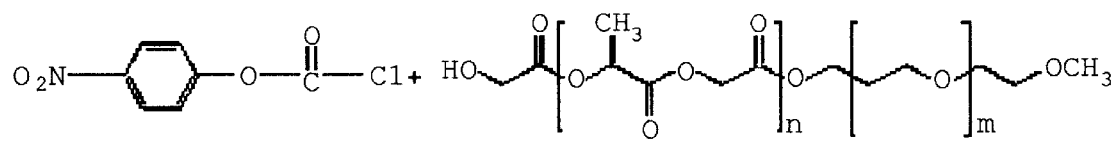
Figure 2:
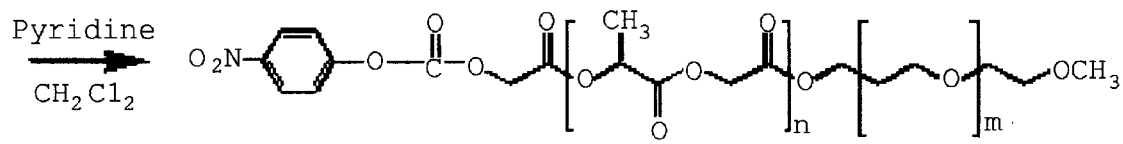
Figure 2:
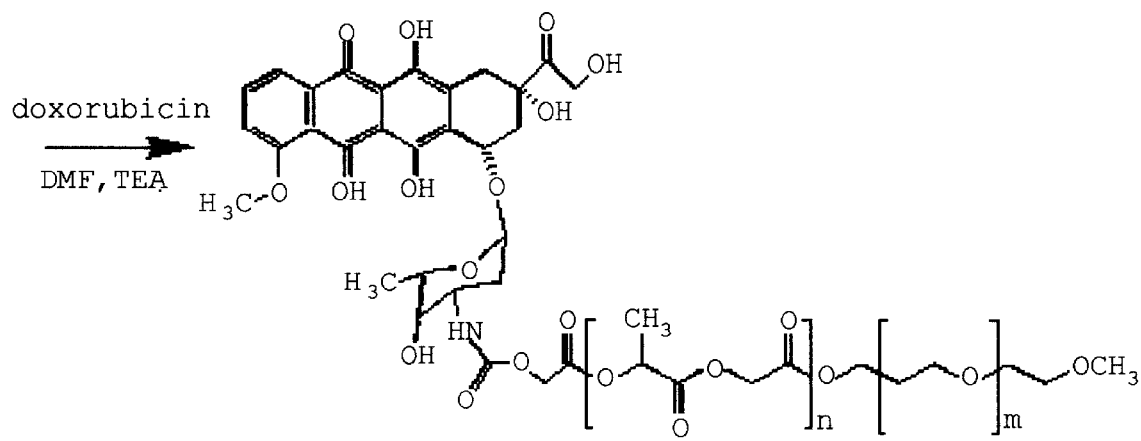

Preparation of Sustained Release Micelles Containing Doxorubicin-conjugated mPEG-PLGA 3 g of mPEG-PLGA obtained above and 80 mg of p-nitrofluoroformate, a linker compound, were dissolved in 30 ml of methylene chloride. Then, 63 mg of pyridine was added to the solution, and reacted for 3 hours under a stream of nitrogen gas. And then, reaction product was precipitated by adding cold diethylether, filtered on a filter paper and dried under a reduced pressure. After dissolving 0.25 g of dried reaction product in 7.5 ml of dimethylformamide, 10 mg of doxorubicin-HCl(Sigma Chem. Co., U.S.A.) and 6.75 mg of triethylamine were added and reacted at room temperature for 24 hours under a nitrogen gas to obtain doxorubicin-conjugated micelle monomer(see: FIG. 2). The said micelle monomers were dispersed in 300 ml of triple distilled water to form doxorubicin-conjugated sustained release micelles, and free doxorubicin was removed by dialyzing the mixture 5 times against 3 L of triple distilled water each time. Doxorubicin-conjugated sustained release micelles were pelletized by ultracentrifugation, and freeze-dried after removing supernatant, and then, stored in the form of doxorubicin-conjugated micelle monomer.

In carrying out the above synthetic reaction, the efficiency of conjugation of doxorubicin to mPEG-PLGA was determined by the ratio of the amount of doxorubicin measured by spectrophotometer after dissolving synthesized micelle monomer in DMSO to the amount of doxorubicin added to the reaction mixture(see: Table 2).

TABLE 2

The efficiency of conjugation of doxorubicin to mPEG-PLGA

| Micelle Monomer | Efficiency of Conjugation | Amount of Cojugation |
|---|---|---|
| DOX-PLGA-mPEG750 | 37.32 (w/w) % | 2.2 (w/w) % |
| DOX-PLGA-mPEG3350 | 36.52 (w/w) % | 2.2 (w/w) % |
| DOX-PLGA-mPEG8000 | 34.22 (w/w) % | 2.2 (w/w) % |

As shown in Table 2 above, the efficiency of conjugation of doxorubicin to mPEG-PLGA was 38(w/w)% and the content of doxorubicin in micelle monomer was 2.2(w/w)%, respectively.

EXAMPLE 3

Figure 3:
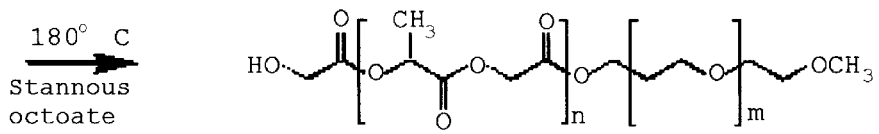
FIG. 3 is a schematic representation of the process for preparing a doxorubicin-conjugated sustained release micelle using hydrazine.
Figure 3:
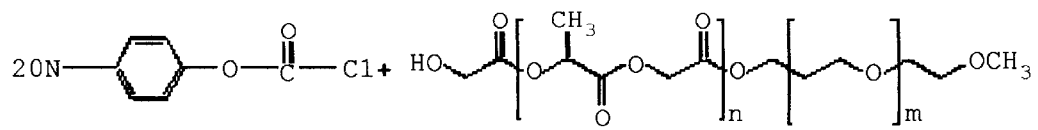
Figure 3:
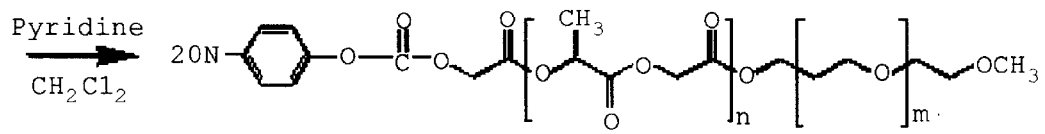
Figure 3:
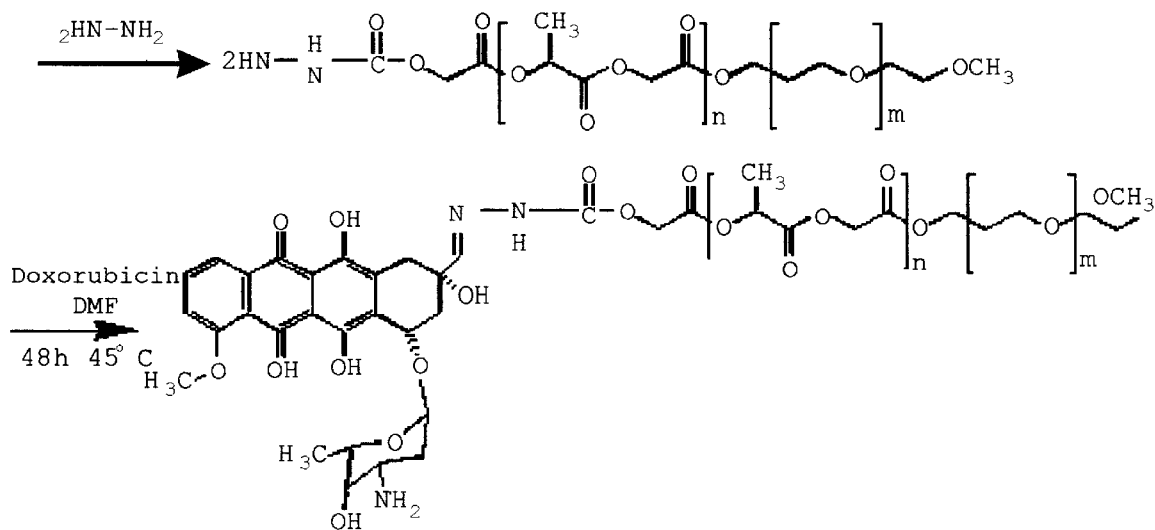

Preparation of Hydrazone Linker-bound mPEG-PLGA 3 g of mPEG-PLGA and 80 mg of p-nitrofluoroformate, a linker compound, were dissolved in 30 ml of methylene chloride. Then, 63 mg of pyridine was added to the solution, and reacted for 3 hours under nitrogen gas. And then, the reaction product was precipitated by adding cold diethylether, filtered, dried, redissolved in methylene chloride, and 2 mg of hyrazine-dissolved methylene chloride solution was added in a dropwise and reacted with continued stirring for 3 hours at room temperature. Cold diethylether was added to precipitate the reaction product, filtered and dried to obtain hydrazone linker-bound mPEG-PLGA(see: FIG. 3 below).

EXAMPLE 4

Preparation of Sustained Release Micelles Containing Conjugate of Doxorubicin and Hydrazone Linker-bound mPEG-PLGA After dissolving 0.25 g of hydrazone linker-bound mPEG-PLGA obtained in Example 3 and 10 mg of doxorubicin-HCl in 7.5 ml of dimethylformamide, conjugation reaction was performed for 24 hours at room temperature under nitrogen gas to obtain doxorubicin-conjugated micelle monomers. The micelle monomers were dispersed in 300 ml of triple distilled water to form doxorubicin-conjugated sustained release micelles, and free doxorubicin was removed by dialyzing the mixture 5 times against 3 L of triple distilled water each time. Doxorubicin-conjugated sustained release micelles were pelletized by ultracentrifugation, and freeze-dried after removing supernatant, and then, stored in the form of doxorubicin-conjugated micelle monomers. The efficiency of conjugation of doxorubicin was determined analogously as in Example 2(see: Table 3 below).

Example 5

Figure 4:
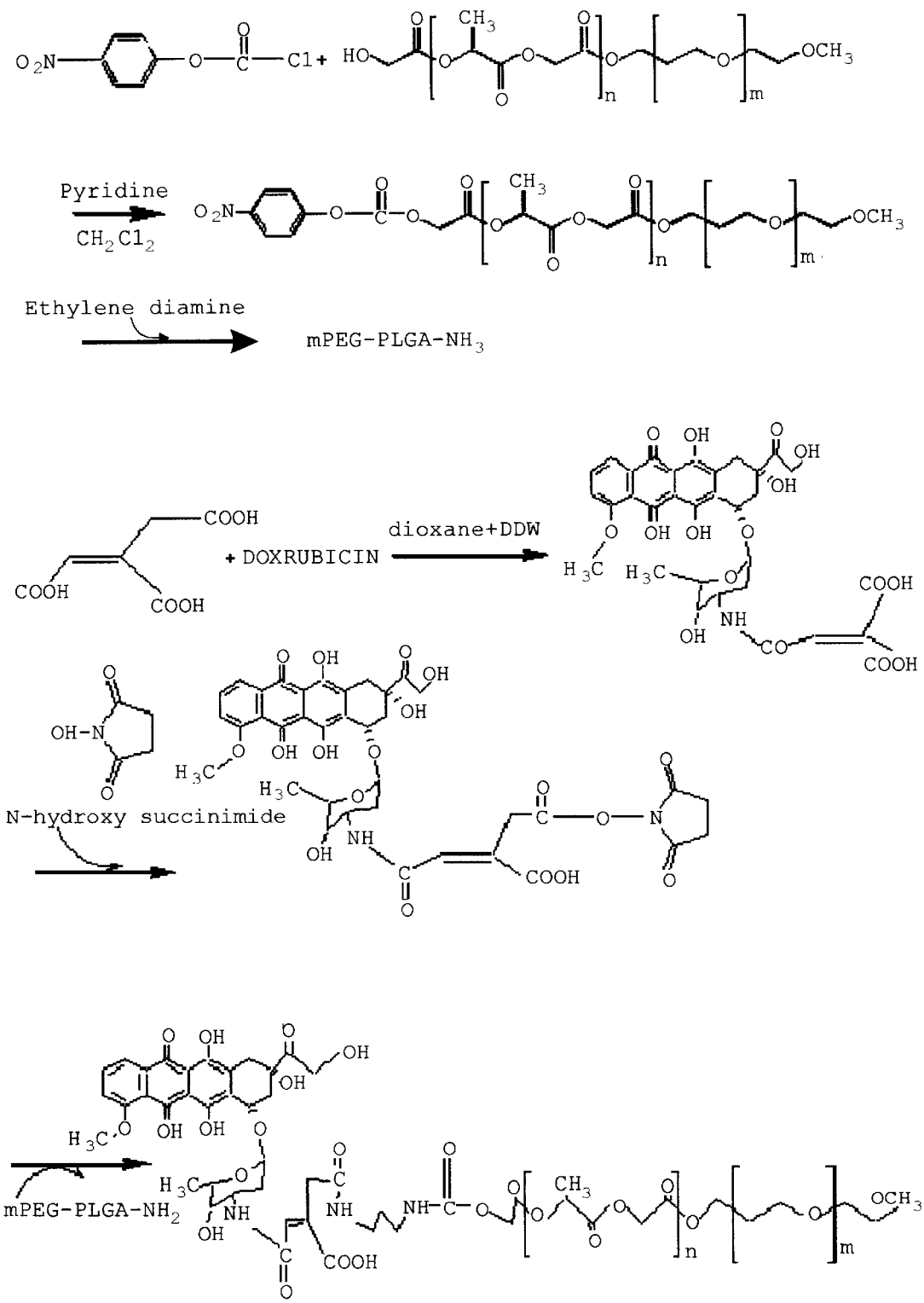
FIG. 4 is a schematic representation of the process for preparing a doxorubicin-conjugated sustained release micelle using cis-aconitic anhydride.

Preparation of Micelles Containing Conjugate of Doxorubicin and Cis-aconitidyl Linker-bound mPEG-PLGA 10 mg of cis-aconitic anhydride dissolved in dioxane was added to 2 ml of 0.1M phosphate buffer solution containing 10 mg of doxorubicin and, left to stand at 0° C. for 10 min and at room temperature for 10 min, and then, diluted with 3 ml of distilled water. Thereafter, 1N hydrochloric acid solution was added at 0° C., to give a precipitate, and centrifuged to obtain the precipitate dissolved in phosphate buffer solution. Acidity of the solution was controlled to pH 8, and obtained cis-aconitidyl doxorubicin. 1.35 mg of hydroxy succinimide, 2.4 mg of dichlorohexylcarbodiimide (DCC), and 3.5 mg of cis-aconitidyl doxorubicin were dissolved in 2 ml of dimethyl formamide(DMF) and reacted for 1 hour at room temperature to activate the said conjugate. In a similar manner as in Example 3, 3 g of mPEG-PLGA and 80 mg of p-nitrofluoroformate, a linker compound, were dissolved in 30 ml of methylene chloride, and 63 mg of pyridine was added to the solution, and then, reacted for 3 hours under nitrogen gas. The reaction product was precipitated by adding cold diethylether to introduce amine group into mPEG-PLGA. 3 g of activated mPEG-PLGA was dissolved in 30 ml of methylene chloride and reacted with 0.2 g of ethylene diamine, and added to cold diethylether to obtain precipitate. After dissolving 0.5 g of activated mPEG-PLGA and 3.5 mg of activated cis-aconitidyl doxorubicin in dimethylformamide(DMF), reaction was performed at room temperature for 12 hours. The reaction product was added to cold diethylether and precipitated finally to obtain doxorubicin-PLGA-mPEG(see: FIG. 4).

TABLE 3

The efficiency of conjugation of doxorubicin to mPEG-PLGA

| Biodegradable Polymer and Drug | Efficiency of Conjugation | Amount of Conjugation |
| --- | --- | --- |
| DOX-PLGA-mPEG750 | 28.32 (w/w) % | 1.7 (w/w) % |
| DOX-PLGA-mPEG3350 | 27.11 (w/w) % | 1.7 (w/w) % |
| DOX-PLGA-mPEG8000 | 26.07 (w/w) % | 1.7 (w/w) % |

As shown in Table 3 above, the efficiency of conjugation of doxorubicin to mPEG-PLGA was 26–29(w/w)%, and the content of doxorubicin in doxorubicin micelle monomer was 1.7(w/w)%.

Example 6

Preparation of Sustained Release Micelle Formulation 100 mg each of doxorbicin-conjugated micelle monomers stored in Examples 2 and 4 was dissolved in 10 ml of acetone, respectively. Then, acetone was evaporated by adding 100 ml each of triple distilled water while stirring for 6 hours to obtain doxorubicin-conjugated sustained release micelle formulation. Depending on molecular weights of mPEG incorporated in micelle monomers, the sizes of doxorubicin-conjugated sustained release micelles prepared above were determined by employing dynamic light scattering(DLS) method(see: Table 4)

TABLE 4

The sizes of doxorubicin-conjugated micelles depending on molecular weights of mPEG

| Sustained Release Micelle | Significant Diameter (nm) |
| --- | --- |
| DOX-PLGA-mPEG750 | 62.0 |
| DOX-PLGA-mPEG3350 | 61.48 |
| DOX-PLGA-mPEG8000 | 66.21 |

As shown in Table 4 above, the sizes of doxorubicin-conjugated sustained release micelles were found to be independent on molecular weights of mPEG.

Example 7

Figure 5:
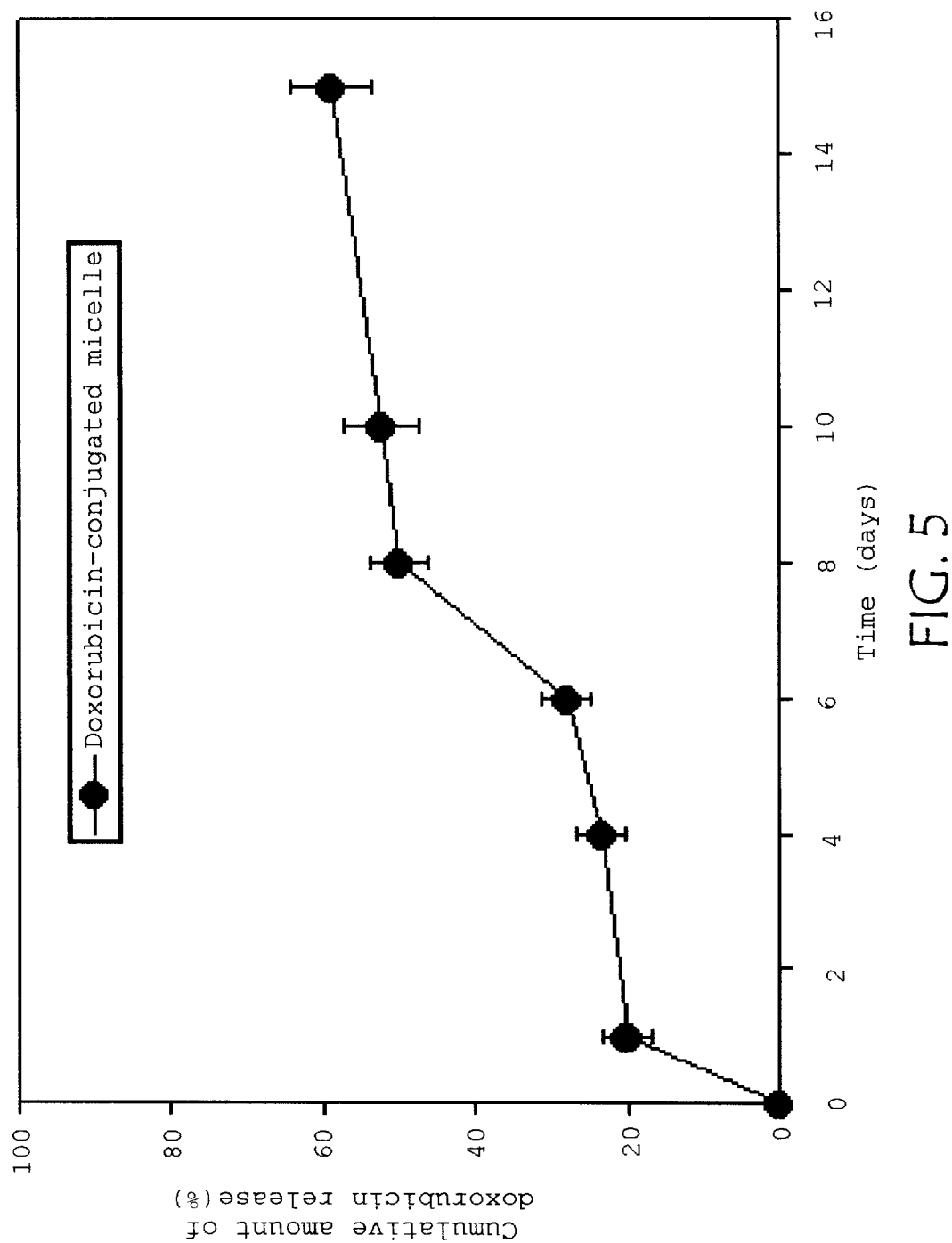
FIG. 5 is a graph showing the time course of the cumulative amount of doxorubicin release.

Measurement of Doxorubicin Release from Doxorubicin-conjugated Sustained Release Micelles 20 ml of phosphate buffer solution(pH 6.5) containing 1 mg/ml of DOX-PLGA-mPEG8000, the doxorubicin-conjugated sustained release micelles prepared in Example 6, was injected into a dialysis bag(10,000 cut-off), which was then placed in 60 ml of the same phosphate buffer solution. With stirring for 16 days at room temperature, samples were taken from the outer buffer solution which contain released doxorubicin through the membrane, and doxorubicin release was detected spectorphotometerically at 480 nm(see: FIG. 5). FIG. 5 is a graph showing the cumulative amount of doxorubicin release with time. As shown in FIG. 5, it has been found that doxorubicin was released slowly for a long period of time from the gradually degrading doxorubicin-conjugated sustained release micelle, since the doxorubicin-conjugated sustained release micelle is consist of a biodegadable polymer which is degraded slowly in nature.

EXAMPLE 8

Effect of Doxorubicin-conjugated Sustained Release Micelle on Cancer Cell

Figure 6:
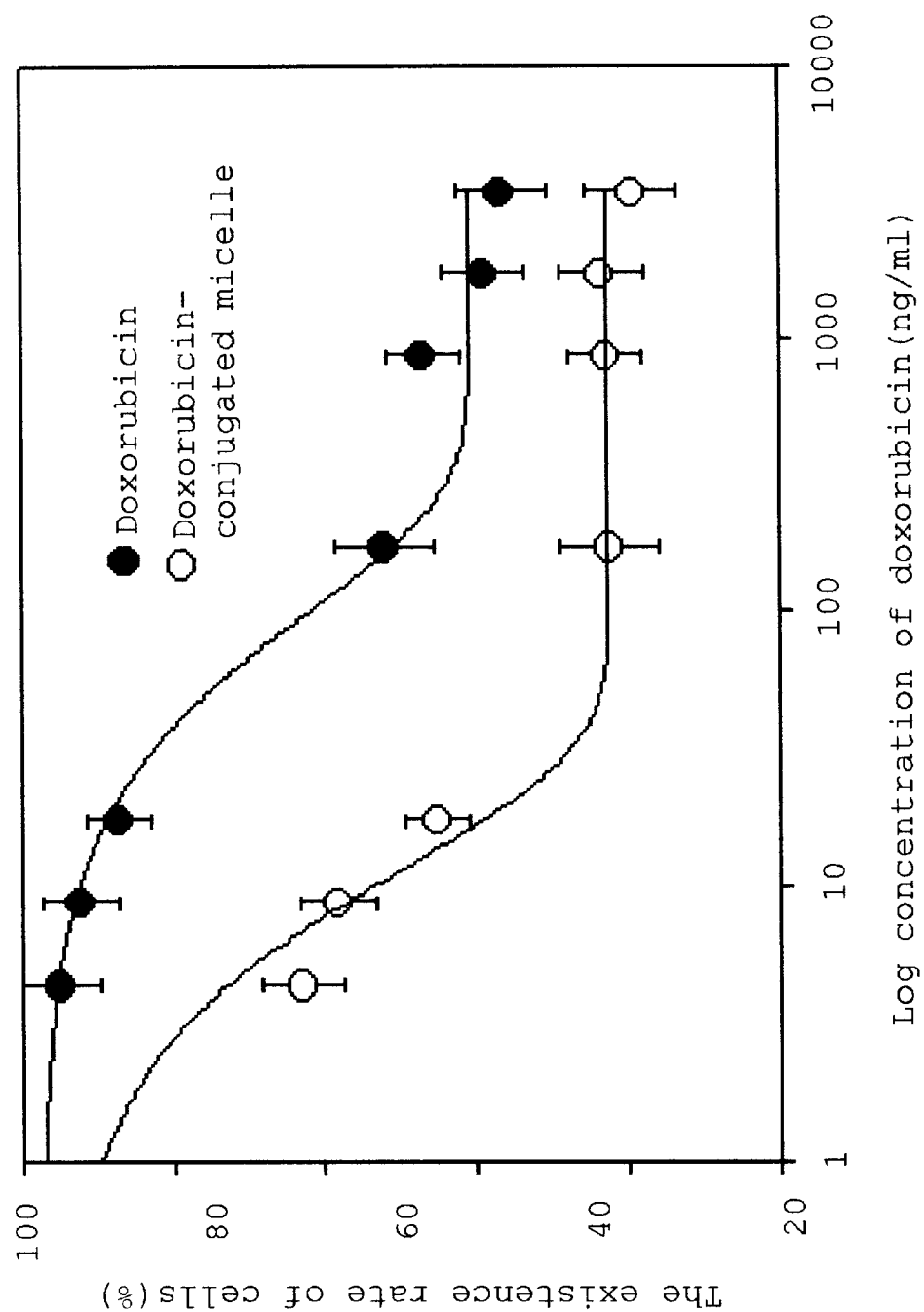
FIG. 6 is a graph showing the comparison of anticancer activities of free doxorubicin and doxorubicin-conjugated sustained release micelle.

In order to examine whether the doxorubicin-conjugated sustained release micelles can be transported into cancer cell more efficiently than free doxorubicin, the doxorubicin-conjugated sustained release micelle prepared in Example 2 was incubated with a hepatoma cell line, HepG2 cell(Korea Cell Line Bank, KCLB, Korea), and cancer cell cytotoxicity of the micelle was investigated employing a fluorocytometry and a microscopy(see: FIG. 6). FIG. 6 is a graph showing the comparison of anticancer activity of free doxorubicin with that of doxorubicin-conjugated sustained release micelle formulation of the invention. As shown in FIG. 6, the doxorubicin-conjugated micelles have been found to enhance anticancer activity than free doxorubicin. Since the doxorubicin-conjugated micelles are likely to be transported into cells by endocytosis, a large amount of doxorubicin can be accumulated within HepG2 cells.

As clearly illustrated and demonstrated above, the present invention provides a process for preparing sustained release micelle by conjugating a biodegradable polymer to a drug such as anticancer agent, and a sustained-release micelle prepared by the process. In accordance with the present invention, the sustained-release micelle prepared by the invention makes possible its practical application in anti-cancer therapy with a high efficieny, by loading a high amount of drug and controlling the release rate of drug.

What is claimed is:

1. A method of preparing a drug delivery composition, comprising:
    providing a substantially linear polymer comprising a hydrophobic portion at one end and a hydrophilic portion at the other end, wherein the hydrophobic portion of the polymer comprises at least one biodegradable polyester section;
    reacting a linker with the polymer so as to connect the linker at a free end of the hydrophobic portion of the polymer; and reacting a pharmaceutically active compound with the linker of the polymer so as to bind the pharmaceutically active compound to the polymer.

2. The method of claim 1, further comprising dispersing the composition in an aqueous liquid medium so as to form micelle of the composition.

3. A method of preparing a drug delivery composition, comprising:
    providing a substantially linear polymer comprising a hydrophobic portion at one end and a hydrophilic portion at the other end, wherein the polymer comprises at least one biodegradable section, wherein the preparation of the polymer comprises copolymerizing a biodegradable polyester polymer and a polyethylene glycol (PEG) polymer;
    reacting a linker with the polymer so as to connect the linker at a free end of the hydrophobic portion of the polymer; and
    reacting a pharmaceutically active compound with the linker of the polymer so as to bind the pharmaceutically active compound to the polymer.

4. The method of claim 3, wherein the polyester polymer is selected from the group consisting of polylactic acid (PLA), polyglycolic acid (PGA), poly(D,L-lactic-co-glycolic acid) (PLGA), poly(caprolactone), poly(valerolactone), poly(hydroxy butyrate) and poly(hydroxy valerate).

5. The method of claim 3, wherein the polyethyleneglycol polymer is substituted with a methoxy group at an end thereof, wherein the methoxy-substituted polymer is methoxypolyethyleneglycol.

6. The method of claim 3, wherein the copolymerization is performed in the presence of stannous octate.

7. The method of claim 3, wherein the copolymerization is performed at a temperature ranged from about 160° C. to about 200° C.

8. The method of claim 3, wherein the copolymerization is performed under a substantially vacuum condition.

9. The method of claim 1, wherein the polymer comprises a functional group at the free end of the hydrophobic portion.

10. The method of claim 9, wherein the functional group comprises a hydroxyl group.

11. The method of claim 10, wherein in the reaction of the linker with the polymer, the linker reacts with the hydroxyl group.

12. The method of claim 1, wherein the linker is selected from the group consisting of p-nitrophenyl chloroformate, carbonyldiimidazole(CDI), N,N'-disuccinimidyl carbonate (DSC), cis-aconitic anhydride, and a mixture of these compounds.

13. The method of claim 1, wherein the reaction of the linker with the polymer is performed in the presence of pyridine and nitrogen.

14. The method of claim 1, wherein before the reaction of the linker with the polymer, the polymer is dissolved in an organic solvent.

15. The method of claim 14, wherein the organic solvent comprises methylene chloride.

16. The method of claim 1, wherein before the reaction with the pharmaceutically active compound, the polymer with the linker is further reacted with hydrazine.

17. The method of claim 1, wherein the pharmaceutically active compound is bonded to the linker by a covalent bond.

18. The method of claim 1, wherein the pharmaceutically active compound comprises an anticancer drug.

19. The method of claim 1, wherein the pharmaceutically active compound is selected from the group consisting of doxorubicin, adriamycin, cisplatin, taxol, and 5-fluorouracil.

20. A drug delivery micelle, comprising a composition prepared by the method of preparing a drug delivery composition, comprising:
   providing a substantially linear polymer comprising a hydrophobic portion at one end and a hydrophilic portion at the other end, wherein the polymer comprises at least one biodegradable section;
   reacting a linker with the polymer so as to connect the linker at a free end of the hydrophobic portion of the polymer; and
   reacting a pharmaceutically active compound with the linker of the polymer so as to bind the pharmaceutically active compound to the polymer.

21. A drug delivery composition, comprising:
   a substantially linear polymer comprising a hydrophobic portion at one end and a hydrophilic portion at the other end, the hydrophobic portion of the polymer comprising at least one biodegradable polyester section;
   a linker portion at a free end of the hydrophobic portion; and
   a pharmaceutically active compound bonded with the linker portion.

22. A drug delivery composition comprising:
   a substantially linear polymer comprising a hydrophobic portion at one end and a hydrophilic portion at the other end, the polymer comprising at least one biodegradable section, wherein the polymer is a block copolymer of a biodegradable polyester polymer and a polyethylene glycol(PEG) polymer;
   a linker portion at a free end of the hydrophobic portion; and
   a pharmaceutically active compound bonded with the linker portion.

23. The drug delivery composition of claim 22, wherein the polyester polymer is selected from the group consisting of polylactic acid (PLA), polyglycolic acid (PGA), poly(D,L-lactic-co-glycolic acid) (PLGA), poly(caprolactone), poly(valerolactone), poly(hydroxy butyrate) and poly(hydroxy valerate).

24. The drug delivery composition of claim 22, wherein the polyethyleneglycol polymer comprises methoxypolyethyleneglycol.

25. The drug delivery composition of claim 21, wherein the linker portion is formed by reacting the polymer and a linker selected from the group consisting of p-nitrophenyl chloroformate, carbonyldiimidazole(CDI), N,N'-disuccinimidyl carbonate(DSC), cis-aconitic anhydride, and a mixture of these compounds.

26. The drug delivery composition of claim 21, wherein the pharmaceutically active compound is bonded to the linker by a covalent bond.

27. The drug delivery composition of claim 21, wherein the pharmaceutically active compound comprises an anticancer drug.

28. The drug delivery composition of claim 21, wherein the pharmaceutically active compound is selected from the group consisting of doxorubicin, adriamycin, cisplatin, taxol, and 5-fluorouracil.

29. A liquid composition comprising a pharmaceutically active compound in a drug delivery composition of claim 21, wherein the drug delivery composition is dispersed in an aqueous medium.

30. A method of using the liquid composition of claim 29, comprising administering the liquid composition to a patient.

31. The method of claim 30, wherein the biodegradable polyester section degrades over an extended period of time.

32. The method of claim 30, wherein the pharmaceutically active compound is released for an extended period of time.

33. The method of claim 30, wherein the pharmaceutically active compound is released for a period longer than 1 day after the administration.

34. The method of claim 30, wherein the pharmaceutically active compound is released for a period up to about 15 days after administration.

35. The method of claim 30, wherein the pharmaceutically active compound comprises an anticancer drug.

36. The method of claim 30, wherein the pharmaceutically active compound comprises doxorubicin.

* * * * *